(12) United States Patent
Savitsky et al.

(10) Patent No.: US 11,631,342 B1
(45) Date of Patent: *Apr. 18, 2023

(54) EMBEDDED MOTION SENSING TECHNOLOGY FOR INTEGRATION WITHIN COMMERCIAL ULTRASOUND PROBES

(71) Applicants: Eric Savitsky, Malibu, CA (US); Dan Katz, Encino, CA (US); Gabriele Nataneli, Beverly Hills, CA (US)

(72) Inventors: Eric Savitsky, Malibu, CA (US); Dan Katz, Encino, CA (US); Gabriele Nataneli, Beverly Hills, CA (US)

(73) Assignee: THE REGENTS OF UNIVERSITY OF CALIFORNIA, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/374,795

(22) Filed: Jul. 13, 2021

Related U.S. Application Data

(63) Continuation of application No. 16/037,796, filed on Jul. 17, 2018, now Pat. No. 11,062,624, which is a continuation of application No. 13/481,725, filed on May 25, 2012, now Pat. No. 10,026,338.

(51) Int. Cl.
G09B 23/28 (2006.01)
A61B 8/00 (2006.01)

(52) U.S. Cl.
CPC .......... *G09B 23/286* (2013.01); *A61B 8/4254* (2013.01)

(58) Field of Classification Search
CPC ............................ G09B 23/286; A61B 8/4254
USPC ........................................................ 600/443
See application file for complete search history.

(56) References Cited

U.S. PATENT DOCUMENTS

| | | | |
|---|---|---|---|
| 1,488,233 A | 3/1924 | Diehl |
| 1,762,937 A | 6/1930 | Staud |
| 2,019,121 A | 10/1935 | Rewal |
| 2,112,019 A | 3/1938 | Gyger |

(Continued)

FOREIGN PATENT DOCUMENTS

| | | | |
|---|---|---|---|
| EP | 1103223 A2 | 5/2001 |
| EP | 2801966 A1 | 11/2014 |

(Continued)

OTHER PUBLICATIONS

Chung, Gregory, "Effects of Simulation-Based Practice on Focused Assessment . . . ", Military Medicine, Oct. 2013, vol. 178.

(Continued)

*Primary Examiner* — Amelie R Davis
*Assistant Examiner* — John Denny Li
(74) *Attorney, Agent, or Firm* — Cislo & Thomas, LLP

(57) ABSTRACT

An ultrasound system including an ultrasound machine and an ultrasound probe. The ultrasound probe includes an ultrasound transducer, ultrasound circuitry, a six degree of freedom (6-DOF) sensor, and a probe housing. The probe housing encases the ultrasound transducer and the 6-DOF sensor. By embedding motion-sensing technology directly within the housing of the ultrasound transducer, the position and orientation of the ultrasound probe can be tracked in an automated manner in relation to an indicator mark on the ultrasound screen. This allows assisting technologies to mitigate human error that arises from misalignment of the transducer indicator.

20 Claims, 4 Drawing Sheets

(56) References Cited

U.S. PATENT DOCUMENTS

| | | |
|---|---|---|
| 2,127,610 A | 8/1938 | Moore |
| 2,705,049 A | 3/1955 | Brooks |
| 2,705,307 A | 3/1955 | Nyswander |
| 2,722,947 A | 11/1955 | Sragal |
| 2,886,316 A | 5/1959 | Ayala |
| 4,040,171 A | 8/1977 | Cline et al. |
| 4,838,863 A | 6/1989 | Allard et al. |
| 4,838,869 A | 6/1989 | Allard |
| 4,994,034 A | 2/1991 | Botich et al. |
| 5,231,381 A | 7/1993 | Duwaer |
| 5,513,992 A | 5/1996 | Refait |
| 5,609,485 A * | 3/1997 | Bergman ............ G09B 23/286 434/262 |
| 5,678,565 A | 10/1997 | Sarvazyan |
| 5,689,443 A | 11/1997 | Ramanathan |
| 5,701,900 A | 12/1997 | Shehada et al. |
| 5,704,791 A | 1/1998 | Gillio |
| 5,755,577 A | 5/1998 | Gillio |
| 5,767,839 A | 6/1998 | Rosenberg |
| 5,776,062 A | 7/1998 | Nields |
| 5,791,908 A | 8/1998 | Gillio |
| 5,800,177 A | 9/1998 | Gillio |
| 5,800,178 A | 9/1998 | Gillio |
| 5,800,179 A | 9/1998 | Bailey |
| 5,800,350 A | 9/1998 | Coppleson et al. |
| 5,827,942 A | 10/1998 | Madsen et al. |
| 5,882,206 A | 3/1999 | Gillio |
| 5,889,237 A | 3/1999 | Makinwa |
| 5,934,288 A | 8/1999 | Avila et al. |
| 6,001,472 A | 12/1999 | Ikeda et al. |
| 6,048,312 A | 4/2000 | Ishrak et al. |
| 6,063,030 A | 5/2000 | Vara et al. |
| 6,068,597 A | 5/2000 | Lin |
| 6,074,213 A | 6/2000 | Hon |
| 6,113,395 A | 9/2000 | Hon |
| 6,117,078 A * | 9/2000 | Lysyansky ............ G01S 15/06 434/262 |
| 6,122,538 A | 9/2000 | Sliwa, Jr. et al. |
| 6,156,213 A | 12/2000 | Dudley et al. |
| 6,193,657 B1 | 2/2001 | Drapkin |
| 6,267,599 B1 | 7/2001 | Bailey |
| 6,468,212 B1 | 10/2002 | Scott et al. |
| 6,502,756 B1 | 1/2003 | F.ang.hraeus |
| 6,511,427 B1 | 1/2003 | Sliwa, Jr. et al. |
| 6,548,768 B1 | 4/2003 | Pettersson et al. |
| 6,570,104 B1 | 5/2003 | Ericson et al. |
| 6,654,000 B2 | 11/2003 | Rosenberg |
| 6,663,008 B1 | 12/2003 | Pettersson et al. |
| 6,665,554 B1 | 12/2003 | Charles et al. |
| 6,666,376 B1 | 12/2003 | Ericson |
| 6,667,695 B2 | 12/2003 | Pettersson et al. |
| 6,674,427 B1 | 1/2004 | Pettersson et al. |
| 6,689,966 B2 | 2/2004 | Wiebe |
| 6,693,626 B1 | 2/2004 | Rosenberg |
| 6,694,163 B1 | 2/2004 | Vining |
| 6,698,660 B2 | 3/2004 | F.ang.hraeus et al. |
| 6,714,213 B1 | 3/2004 | Lithicum et al. |
| 6,714,901 B1 | 3/2004 | Cotin et al. |
| 6,719,470 B2 | 4/2004 | Berhin |
| 6,722,574 B2 | 4/2004 | Skantze et al. |
| 6,732,927 B2 | 5/2004 | Olsson et al. |
| 6,750,877 B2 | 6/2004 | Rosenberg et al. |
| 6,780,016 B1 | 8/2004 | Toly |
| 6,816,148 B2 | 11/2004 | Mallett et al. |
| 6,836,555 B2 | 12/2004 | Ericson et al. |
| 6,854,821 B2 | 2/2005 | Ericson et al. |
| 6,864,880 B2 | 3/2005 | Hugosson et al. |
| 6,878,062 B2 | 4/2005 | Bjorklund et al. |
| 6,896,650 B2 | 5/2005 | Tracey et al. |
| 6,916,283 B2 | 7/2005 | Tracey et al. |
| 6,927,916 B2 | 8/2005 | Craven-Bartle |
| 6,929,183 B2 | 8/2005 | Pettersson |
| 6,929,481 B1 | 8/2005 | Alexander et al. |
| 6,947,033 B2 | 9/2005 | F.ang.hraeus et al. |
| 6,958,747 B2 | 10/2005 | Sahlberg et al. |
| 6,966,495 B2 | 11/2005 | Lynggaard et al. |
| 6,992,655 B2 | 1/2006 | Ericson et al. |
| 7,002,559 B2 | 2/2006 | Ericson |
| 7,035,429 B2 | 4/2006 | Andreasson |
| 7,037,258 B2 | 5/2006 | Chatenever et al. |
| 7,050,653 B2 | 5/2006 | Edso et al. |
| 7,054,487 B2 | 5/2006 | Ericson et al. |
| 7,072,529 B2 | 7/2006 | Hugosson et al. |
| 7,089,308 B2 | 8/2006 | Fransson et al. |
| 7,094,977 B2 | 8/2006 | Ericson et al. |
| 7,110,604 B2 | 9/2006 | Olsson |
| 7,120,320 B2 | 10/2006 | Petterson et al. |
| 7,121,465 B2 | 10/2006 | Rignell |
| 7,127,682 B2 | 10/2006 | Sandstrom et al. |
| 7,143,952 B2 | 12/2006 | Ericson |
| 7,145,556 B2 | 12/2006 | Pettersson |
| 7,154,056 B2 | 12/2006 | Bergqvist et al. |
| 7,162,087 B2 | 1/2007 | Bryborn |
| 7,167,164 B2 | 1/2007 | Ericson et al. |
| 7,172,131 B2 | 2/2007 | Pettersson et al. |
| 7,175,095 B2 | 2/2007 | Pettersson et al. |
| 7,176,896 B1 | 2/2007 | Fahraeus et al. |
| 7,180,509 B2 | 2/2007 | Fermgard et al. |
| 7,195,166 B2 | 3/2007 | Olsson et al. |
| 7,202,861 B2 | 4/2007 | Lynggaard |
| 7,202,963 B2 | 4/2007 | Wiebe et al. |
| 7,239,306 B2 | 7/2007 | Fahraeus et al. |
| 7,246,321 B2 | 7/2007 | Bryborn et al. |
| 7,248,250 B2 | 7/2007 | Pettersson et al. |
| 7,249,256 B2 | 7/2007 | Hansen et al. |
| 7,249,716 B2 | 7/2007 | Bryborn |
| 7,254,839 B2 | 8/2007 | Fahraeus et al. |
| 7,278,017 B2 | 10/2007 | Skantze |
| 7,281,668 B2 | 10/2007 | Pettersson et al. |
| 7,283,676 B2 | 10/2007 | Olsson |
| 7,293,697 B2 | 11/2007 | Wiebe et al. |
| 7,295,193 B2 | 11/2007 | Fahraeus |
| 7,296,075 B2 | 11/2007 | Lynggaard |
| 7,321,692 B2 | 1/2008 | Bryborn et al. |
| 7,333,947 B2 | 2/2008 | Wiebe et al. |
| 7,345,673 B2 | 3/2008 | Ericson et al. |
| 7,353,393 B2 | 4/2008 | Hansen et al. |
| 7,356,012 B2 | 4/2008 | Wiebe et al. |
| 7,371,068 B2 | 5/2008 | Lloyd et al. |
| 7,382,361 B2 | 6/2008 | Burstrom et al. |
| 7,385,595 B2 | 6/2008 | Bryborn et al. |
| 7,408,536 B2 | 8/2008 | Hugosson et al. |
| 7,415,501 B2 | 8/2008 | Burstrom |
| 7,418,160 B2 | 8/2008 | Lynggaard |
| 7,422,154 B2 | 9/2008 | Ericson |
| 7,441,183 B2 | 10/2008 | Burstrom et al. |
| 7,457,413 B2 | 11/2008 | Thuvesholmen et al. |
| 7,457,476 B2 | 11/2008 | Olsson |
| 7,543,753 B2 | 6/2009 | Pettersson |
| 7,588,191 B2 | 9/2009 | Pettersson et al. |
| 7,600,693 B2 | 10/2009 | Pettersson |
| 7,649,637 B2 | 1/2010 | Wiebe et al. |
| 7,670,070 B2 | 3/2010 | Craven-Bartle |
| 7,672,513 B2 | 3/2010 | Bjorklund et al. |
| 7,701,446 B2 | 4/2010 | Sahlberg et al. |
| 7,710,408 B2 | 5/2010 | Ericson |
| 7,751,089 B2 | 7/2010 | Fahraeus et al. |
| 7,753,283 B2 | 7/2010 | Lynggaard |
| 7,777,777 B2 | 8/2010 | Bowman et al. |
| 7,788,315 B2 | 8/2010 | Johansson |
| 7,794,388 B2 | 9/2010 | Draxinger et al. |
| 7,806,696 B2 | 10/2010 | Alexander et al. |
| 7,833,018 B2 | 11/2010 | Alexander et al. |
| 7,850,454 B2 | 12/2010 | Toly |
| 7,857,626 B2 | 12/2010 | Toly |
| 7,871,850 B2 | 1/2011 | Park |
| 7,931,470 B2 | 4/2011 | Alexander et al. |
| 8,244,506 B2 | 8/2012 | Butsev et al. |
| 8,294,972 B2 | 10/2012 | Chung |
| 8,428,326 B2 | 4/2013 | Falk et al. |
| 8,480,404 B2 | 7/2013 | Savitsky |
| 8,480,406 B2 | 7/2013 | Alexander et al. |
| 8,556,635 B2 | 10/2013 | Toly |
| 8,721,344 B2 | 5/2014 | Marmaropoulos et al. |

(56) References Cited

U.S. PATENT DOCUMENTS

| | | |
|---|---|---|
| 9,128,116 B2 | 9/2015 | Welch et al. |
| 9,251,721 B2 | 2/2016 | Lampotang |
| 9,436,993 B1 | 9/2016 | Stolka et al. |
| 9,870,721 B2 | 1/2018 | Savitsky et al. |
| 9,911,365 B2 | 3/2018 | Siassi |
| 10,052,010 B2 | 8/2018 | Feddema |
| 10,132,015 B2 | 11/2018 | Woodruff et al. |
| 11,011,077 B2 | 5/2021 | Garcia Kilroy |
| 2001/0031920 A1 | 10/2001 | Kaufman et al. |
| 2002/0076581 A1 | 6/2002 | McCoy |
| 2002/0076681 A1 | 6/2002 | Leight et al. |
| 2002/0088926 A1 | 7/2002 | Prasser |
| 2002/0099310 A1 | 7/2002 | Kimchy et al. |
| 2002/0168618 A1 | 11/2002 | Anderson et al. |
| 2002/0173721 A1 | 11/2002 | Grunwald et al. |
| 2004/0043368 A1 | 3/2004 | Hsieh et al. |
| 2004/0087850 A1 | 5/2004 | Okerlund et al. |
| 2005/0119569 A1 | 6/2005 | Ohtake |
| 2005/0181342 A1* | 8/2005 | Toly ................ G09B 23/30 434/262 |
| 2005/0214726 A1 | 9/2005 | Feygin et al. |
| 2005/0228617 A1 | 10/2005 | Kerwin et al. |
| 2005/0283075 A1 | 12/2005 | Ma et al. |
| 2006/0020204 A1 | 1/2006 | Serra et al. |
| 2006/0098010 A1 | 5/2006 | Dwyer et al. |
| 2007/0088213 A1 | 4/2007 | Poland |
| 2007/0161904 A1 | 7/2007 | Urbano |
| 2007/0232907 A1 | 10/2007 | Pelissier et al. |
| 2007/0236514 A1 | 10/2007 | Agusanto |
| 2007/0238085 A1 | 10/2007 | Colvin et al. |
| 2008/0009743 A1 | 1/2008 | Hayasaka |
| 2008/0137071 A1 | 6/2008 | Chow |
| 2008/0187896 A1 | 8/2008 | Savitsky |
| 2008/0200807 A1 | 8/2008 | Wright et al. |
| 2008/0204004 A1 | 8/2008 | Anderson |
| 2008/0269606 A1 | 10/2008 | Matsumura |
| 2008/0294096 A1 | 11/2008 | Uber et al. |
| 2008/0312884 A1 | 12/2008 | Hostettler et al. |
| 2009/0006419 A1 | 1/2009 | Savitsky |
| 2009/0043195 A1 | 2/2009 | Poland |
| 2009/0046912 A1 | 2/2009 | Hostettler |
| 2009/0124906 A1* | 5/2009 | Caluser ............. A61B 8/4254 600/443 |
| 2009/0130642 A1 | 5/2009 | Tada et al. |
| 2009/0209859 A1 | 8/2009 | Tsujita et al. |
| 2009/0266957 A1 | 10/2009 | Cermak |
| 2009/0305213 A1 | 12/2009 | Burgkart et al. |
| 2009/0311655 A1 | 12/2009 | Karkanias et al. |
| 2010/0055657 A1 | 3/2010 | Goble et al. |
| 2010/0104162 A1 | 4/2010 | Falk et al. |
| 2010/0179428 A1* | 7/2010 | Pedersen ............. G09B 23/286 600/443 |
| 2010/0268067 A1 | 10/2010 | Razzaque et al. |
| 2010/0277422 A1 | 11/2010 | Muresianu et al. |
| 2011/0010023 A1 | 1/2011 | Kunzig et al. |
| 2011/0306025 A1 | 12/2011 | Sheehan et al. |
| 2012/0021993 A1 | 1/2012 | Kim et al. |
| 2012/0058457 A1 | 3/2012 | Savitsky |
| 2012/0143142 A1 | 6/2012 | Klein |
| 2012/0150783 A1 | 6/2012 | Landy et al. |
| 2012/0179039 A1 | 7/2012 | Pelissier et al. |
| 2012/0200977 A1 | 8/2012 | Nestler |
| 2012/0219937 A1 | 8/2012 | Hughes et al. |
| 2012/0237102 A1 | 9/2012 | Savitsky et al. |
| 2012/0237913 A1 | 9/2012 | Savitsky et al. |
| 2012/0238875 A1 | 9/2012 | Savitsky et al. |
| 2012/0251991 A1 | 10/2012 | Savitsky et al. |
| 2013/0046523 A1 | 2/2013 | Van Dinther |
| 2013/0064036 A1 | 3/2013 | Lee et al. |
| 2013/0065211 A1 | 3/2013 | Amso et al. |
| 2013/0137989 A1 | 5/2013 | Chen |
| 2013/0158411 A1 | 6/2013 | Miyasaka |
| 2013/0179306 A1 | 7/2013 | Want et al. |
| 2013/0236872 A1 | 9/2013 | Laurusonis et al. |
| 2014/0087347 A1 | 3/2014 | Tracy |
| 2014/0114194 A1 | 4/2014 | Kanayama et al. |
| 2014/0119645 A1 | 5/2014 | Zimet |
| 2014/0120505 A1 | 5/2014 | Rios et al. |
| 2014/0170620 A1 | 6/2014 | Savitsky et al. |
| 2014/0228685 A1 | 8/2014 | Eelbode |
| 2014/0272878 A1 | 9/2014 | Shim et al. |
| 2015/0056591 A1 | 2/2015 | Tepper et al. |
| 2015/0078639 A1 | 3/2015 | Hausotte |
| 2015/0084897 A1 | 3/2015 | Nataneli et al. |
| 2015/0086956 A1 | 3/2015 | Savitsky et al. |
| 2015/0140538 A1 | 5/2015 | Savitsky et al. |
| 2015/0154890 A1 | 6/2015 | Savitsky et al. |
| 2015/0213731 A1 | 7/2015 | Sato |
| 2016/0104393 A1 | 4/2016 | Savitsky et al. |
| 2016/0259424 A1 | 9/2016 | Nataneli et al. |
| 2016/0314715 A1 | 10/2016 | Savitsky et al. |
| 2016/0314716 A1 | 10/2016 | Grubbs |
| 2016/0328998 A1 | 11/2016 | Pedersen et al. |
| 2017/0018204 A1 | 1/2017 | Savitsky et al. |
| 2017/0028141 A1 | 2/2017 | Fiedler et al. |
| 2017/0035517 A1 | 2/2017 | Geri |
| 2017/0046985 A1 | 2/2017 | Hendrickson et al. |
| 2017/0110032 A1 | 4/2017 | O'Brien |
| 2017/0270829 A1 | 9/2017 | Bauss |
| 2017/0352294 A1 | 12/2017 | Nataneli et al. |
| 2018/0137784 A1 | 5/2018 | Savitsky et al. |
| 2018/0197441 A1 | 7/2018 | Rios |
| 2018/0211563 A1 | 7/2018 | Savitsky et al. |
| 2018/0330635 A1 | 11/2018 | Savitsky et al. |
| 2018/0366034 A1 | 12/2018 | Casals Gelpi |
| 2019/0057620 A1 | 2/2019 | Eggert |
| 2019/0231436 A1 | 8/2019 | Panse |
| 2019/0321657 A1 | 10/2019 | Hale |
| 2019/0371204 A1 | 12/2019 | Savitsky et al. |
| 2020/0126449 A1 | 4/2020 | Horst |
| 2020/0138518 A1 | 5/2020 | Lang |
| 2020/0242971 A1 | 7/2020 | Wang et al. |
| 2020/0242972 A1 | 7/2020 | Petrinec et al. |
| 2021/0128125 A1 | 5/2021 | Sitti et al. |
| 2021/0134186 A1 | 5/2021 | Savitsky et al. |
| 2021/0186311 A1 | 6/2021 | Levy et al. |

FOREIGN PATENT DOCUMENTS

| | | |
|---|---|---|
| RU | 2127610 C1 | 3/1999 |
| RU | 1994040171 | 11/2014 |
| WO | 2006060406 A1 | 6/2006 |

OTHER PUBLICATIONS

Aligned Management Associates, Inc., Corporate home page describing organizing committee, overview, Procedicus MIST[trademark]-suturing module 30.0, 6 pgs., obtained from website Sep. 6, 2004.

American Academy of Emergency Medicine, conference: 11th annual scientific assembly preconference ultrasound courts, http://www.aaem.org/education/scientificassembly/sa05/precon/ultrasound.shtml, 6 pgs, obtained from website Feb. 16, 2005.

Barbosa, J. et al., "Computer education in emergency medicine residency programs," http://www.med-ed-online.org/res00002.htm, 8 pgs, obtained from website Sep. 6, 2004.

Brannam, Let al, "Emergency nurses utilization of ultrasound guidance for placement of peripheral intravenous lines in difficult-access patients," Acad Emerg Med, 11(12):1361-1363, Dec. 2004.

Calvert, N. et al., "The effectiveness and cost-effectiveness of ultrasound locating devices for central venous access: a systematic review and economic evaluation/executive summary," Health Tech Assess 2003, 7(12), 4 pgs.

Center for Human Simulation, corporate home page describing overview/people, http://www.uchsc.edu, 7 pgs, obtained from website Sep. 6, 2004.

CIMIT News, "The medical access program: new CIMIT initiative to benefit underserved patients/partners telemedicine and CIMIT launch new initiative: stay connected, be healthy/highlights: operating room of the future plug-and-play project," http://www.cimit.org, Jan. 2005; Vol. (2), 2 pgs., obtained from website Mar. 1, 2005.

(56) References Cited

OTHER PUBLICATIONS

Colt, H. G. et al., "Virtual reality bronchoscopy simulation: a revolution in procedural training," Chest 2001; 120:1333-1339.
Computer Motion, "About computer motion: technology to enhance surgeons capabilities, improve patient outcomes and reduce healthcare costs/corporate alliances/products solutions for surgical innovation/training on the da Vinci[registered] surgical system-introduction," 2002 Computer Motion, http://www.computermotion.com, 6 pgs.
Delp, Setal, "Surgical simulation—an emerging technology for training in emergency medicine," Presence, 6(2):147-159, Apr. 1997 (abstract).
Dorner, R. et. al., "Synergies between interactive training simulations and digital storytelling: a component-based framework," Computer Graphics, 26(1):45-55, Feb. 2002 (abstract).
Duque, D. and Kessler S., "Ultrasound guided vascular access," Amer Coli Emerg Phy., http://www.nyacep.org/education/articles/ultrasound%20vascular%20access.htm, 2 pgs, obtained from website May 11, 2005.
Espinet, A. and Dunning J., "Does ultrasound-guided central line insertion reduce complications and time to placement in elective patients undergoing cardiac surgery," Inter Cardiovascular Thoracic Surg, 3:523-527, 2004; http://licvts.ctsnetjournals.org/cgi/content/full/3/3/523, 6 pgs, obtained from website May 11, 2005 (abstract).
Gallagher, A. G. et al., "Virtual reality training for the operating room and cardiac catheterization laboratory," Lancet, 364:1538-1540, Oct. 23, 2004.
Gallagher, A. G. et al., "Psychomotor skills assessment in practicing surgeons experienced in performing advanced laparoscopic procedures," AM Coli Surg, 197(3):479-488, Sep. 2003.
Gausche, M. et. al., "Effect on out-of-hospital pediatric endotracheal intubation on survival and neurological outcome: a controlled clinical trial," JAMA, 283(6):783-790, Feb. 9, 2000.
Gore, D. C. and Gregory, S. R., "Historical perspective on medical errors: Richard Cabot and the Institute of Medicine," J Amer Coli Surg, 197(4), 5 pgs, Oct. 2003.
Grantcharov, T. P. et. al., "Randomized clinical trial of virtual reality simulation for laparoscopic skills training," Br J Surg, 91(2):146-150, Feb. 1, 2004 (abstract).
Grantcharov, T. P. et al., "Learning curves and impact of previous operative experience on performance on a virtual reality simulator to test laparoscopic surgical skills," Am J Surg, 185(2):146-149, Feb. 1, 2004 (abstract).
Haluck, R. S., et al., "Are surgery training programs ready for virtual reality A survey of program directors in general surgery," Arch Surg, 135(7):786-792, Jul. 1, 2000.
Helmreich, R. L., "On error management: lessons from aviation," BMJ, 320:781-785, Mar. 2000.
Huckman, R. S. and Pisano, G. P., "Turf battles in coronary revascularization," N Engl J Med, http://www.nejm.org, 4 pgs, 352(9):857-859, Mar. 3, 2005.
Immersion Corporation, URL: http://www.immersion.com/corporate/products/, corporate home page describing Immersions surgical training simulators—"Wireless Data Glove: The CyberGiove[registered]II System," 5 pgs, obtained from the website Nov. 17, 2005 and Jan. 24, 2008.
injuryboard.com, "Reducing complications associated with central vein catheterization," URSL: http://www.injuryboard.com/view.cfm/Article=668, 5 pgs, obtained from website May 11, 2005.
Intersense, home page listing motion tracking products, http://www.isense.com/prodcuts.aspxid=42 , 1 pg, obtained from website Jan. 24, 2008.
Jemmett, M. E., et al., "Unrecognized misplacement of endotracheal tubes in a mixed urban to rural emergency medical services setting," Acad Emerg Med, 10(9):961-964, Sep. 2003.
Katz, S. H. and Falk, J. L., "Misplaced endotrachial tubes by paramedics in an urban medical services system," Annals Emerg Med, 37:32-37, Jan. 2001.
Lewis, R., "Educational research: time to reach the bar, not lower it," Acad Emerg Med, 12(3):247-248, Mar. 2005.
Liu, A. et, al., "A survey of surgical simulation: applications, technology, and education," Presence, 12(6):1-45, Dec. 2003.
Manchester Visulations Centre, "Webset project-bringing 3D medical training tools to the WWW," http://www.sve.man.ac.uklmvc/research/previous/website, 3 pgs, obtained from the website Sep. 8, 2004.
McLellan, H., "Virtual realities," Mclellan Wyatt Digital, 33 pgs.
Medical Simulation Corporation, corporate home page describing management team/frequently asked questions, http://www.medsimulation.com/about_msc/key_employees.asp, 7 pgs, obtained from website Nov. 25, 2004.
Medtronic, "The StealthStation[registered] treatment guidance system," the corporate home page describing the company fact sheet and profile; http://www.medtronic.com/Newsroom, 4 pgs, obtained from website Mar. 5, 2005.
Mort, T. C., "Emergency tracheal intubation: complications associated with repeated laryngoscopic attempts," Anesth Analg, 99(2):607-613, Aug. 2004, 1 pg, obtained from website Sep. 8, 2004 (abstract).
Nazeer, S. R., et al., "Ultrasound-assisted paracentesis performed by emergency physicians v.s. the traditional technique: a prospective, randomized study," Amer J of Emer Med, 23:363-367, 2005.
NCA Medical Simulation Center, Tutorial-simulation for medical training, http://Simcen.usuhs.millmiccaie, 4 pgs, 2003.
Next Dimension Imaging, "Products-Anatomy Analyzer 2," http://www.nexted.com/anatomyanalyzer.asp, 2 pgs, obtained from website Dec. 7, 2004.
Norris, T. E. et al., "Teaching procedural skills," J General Internal Med, 12(S2):S64-S70, Apr. 1997.
On the Net Resources—Education and Training, URL: http://www.hitl.washington.edu/projects/knowledge_base/education.html, corporate home page regarding internet sites regarding education and training, 16 pgs, obtained from website Jan. 8, 2005.
Osberg, K. M., "Virtual reality and education: a look at both sides of the sword," http://www.hitl.washington.edu/publications/r-93-7/, 19 pgs, Dec. 14, 1992, obtained from website Jan. 21, 2008.
Osmon, S. et al., "Clinical investigations: reporting of medical errors: an intensive care unit experience," Grit Care Med, 32(3), 13 pgs, Mar. 2004.
Ponder, M., et al., "Immersive VR decision training: telling interactive stories featuring advanced human simulation technologies," Eurographics Association 2003, 10 pgs.
Primal, corporate home page describing resources for teaching healthcare practitioners, 2 pgs, obtained from website.
Prystowsky, J. B. et al., "A virtual reality module for intravenous catheter placement," Am J Surg 1999; 177(2): 171-175 (abstract).
Reachin, "Medical Training Development Centre/Reachin technologies AB has entered into a corporation with Mentice AB," Jan. 20, 2004, 4 pgs, obtained from website Nov. 9, 2004.
Rothschild, J. M., "Ultrasound guidance of central vein catheterization," NCBI, Nat Lib Med, www.ncbi.nlm.nih.gov/books/, HSTAT 21, 6 pgs, obtained from website May 11, 2005.
Rowe, R. and Cohen, R. A., "An evaluation of a virtual reality airway simulator," Anesth Analg 2002, 95:62-66,.
Sensable Technologies, "PHANTOM Omni Haptic Device," 2 pgs, http://www.sensable.com/haptic-ohantom-omni.htm., obtained from website Jan. 24, 2008.
Shaffer, K., "Becoming a physician: teaching anatomy in a digital age," NEJM, Sep. 23, 2004; 351(13):1279-81 (extract of first 100 words—no abstract).

\* cited by examiner

EMBEDDED MOTION SENSING TECHNOLOGY FOR INTEGRATION WITHIN COMMERCIAL ULTRASOUND PROBES

CROSS-REFERENCES TO RELATED APPLICATIONS

This patent application is a continuation of U.S. patent application Ser. No. 16/037,796 filed Jul. 17, 2018 for Embedded Motion Sensing Technology for Integration within Commercial Ultrasound Probes, which is a continuation of U.S. patent application Ser. No. 13/481,725 filed May 25, 2012 for Embedded Motion Sensing Technology for Integration within Commercial Ultrasound Probes, which applications are incorporated in their entirety here by this reference.

TECHNICAL FIELD

This invention relates to ultrasound probes, ultrasound probe systems, and ultrasound probe training systems.

BACKGROUND ART

Medical ultrasound hardware utilizes a mechanical transducer to broadcast high-frequency acoustic waves through the human body and then measure the reflection as a means for imaging. To use ultrasound imaging in the clinical setting, ultrasound operators must follow a strict convention to ensure that the image is oriented appropriately and the underlying anatomy is diagnosed correctly. By convention, the transducer is marked with a protruding indicator that must be oriented towards a patient's head or anatomic-right side during scanning. To aid guidance, a matching probe indicator icon is displayed on the screen of the ultrasound machine as a reference (generally on the left side of the screen). Maintaining this strict orientation takes on added significance when performing image-guided interventions (e.g., needle insertion), which may result in catastrophic implications if not performed correctly. For instance, a common pitfall, especially for novice users, is to inadvertently reverse the indicator default setting and erroneously orient the transducer as they are performing an incorrectly oriented, image-guided medical intervention.

However, by embedding motion-sensing technology directly within the housing of the ultrasound transducer (ultrasound probe), the position and orientation of the device can be tracked in relation to an indicator mark on the ultrasound screen in an automated manner, allowing assisting technologies to mitigate human error that arises from misalignment of the transducer indicator. As an example, motion sensors can be used to detect misalignment and provide visual or auditory alerts to notify the user about the probe indicator alignment (e.g., a probe indicator icon moves along the ultrasound screen in relation to the actual probe's orientation relative to a patient's body-rather than a preset position).

Furthermore, motion sensing hardware is employed by commercial solutions that provide real-time or just-in-time refresher training of ultrasound skills in a simulated environment. These simulators employ a motion-controlled handheld device in the shape of an ultrasound probe to recreate the experience of using a real device on a wide selection of pre-recorded patient cases with or without serious clinical pathologies. However, these simulators are currently only available as dedicated workstations or software packages for personal computers (PCs) and require an ad hoc external handheld motion sensing peripheral device for control. As a result, it is not possible to currently integrate the benefits of ultrasound training simulators within a real ultrasound device. The addition of an embedded motion sensor directly inside an ultrasound transducer will make this possible.

Having motion-sensing technology embedded directly within the housing of an ultrasound transducer will enable ultrasound devices to operate in two separate modes: a standard mode that allows the user to scan real patients using the traditional physics of ultrasound as is done currently, and a training mode that will instead allow the user to employ the same ultrasound probe as a motion sensing peripheral to navigate a multitude of existing patient cases augmented with annotations that help the operator expand and refine his or her knowledge of ultrasound imaging.

A typical handheld motion sensor utilizes various sensing components to measure displacement and orientation in three-dimensional (3D) space. While many technologies exist for tracking motion in space, inertial solutions allow the sensor package to retain a small form factor and work without needing additional external components to act as a fixed point of reference. Most inertial solutions combine accelerometers, gyroscopes, and a magnetometer in a single package to measure inertial motion and relate the orientation of the device with respect to the gravity vector and the earth's magnetic field. Whereas it has been previously proposed that this technology reside in a plastic casing of its own, it is now proposed that the electronic hardware be embedded and integrated within the plastic housing of current medical ultrasound transducers.

Also, to improve the fidelity of the simulation in training mode, an additional sensor (a "6+1 DOF" sensor) may be added to the embedded package for measuring compression, allowing the user to investigate the elastic properties of the underlying anatomy in the simulated environment by pressing the tip of the device against a surface with varying amounts of force.

DISCLOSURE OF INVENTION

Accordingly, the present invention can be described generally as an ultrasound system that includes an ultrasound machine and an ultrasound probe. The ultrasound machine displays an ultrasound image, and the ultrasound probe communicates with the ultrasound machine. The ultrasound probe includes an ultrasound transducer, ultrasound circuitry, a six degree of freedom (6-DOF) sensor, and a probe housing. The probe housing encases the ultrasound transducer and the 6-DOF sensor.

The ultrasound transducer transmits acoustic waves and measures the reflected waves to produce a reflected wave signal. The ultrasound circuitry receives the reflected wave signal from the ultrasound transducer and transmits an image signal to the ultrasound machine. The 6-DOF sensor measures the position and orientation of the ultrasound probe. Accordingly, the position and the orientation of the ultrasound probe may be tracked.

BEST MODE FOR CARRYING OUT THE INVENTION

Figure 1:
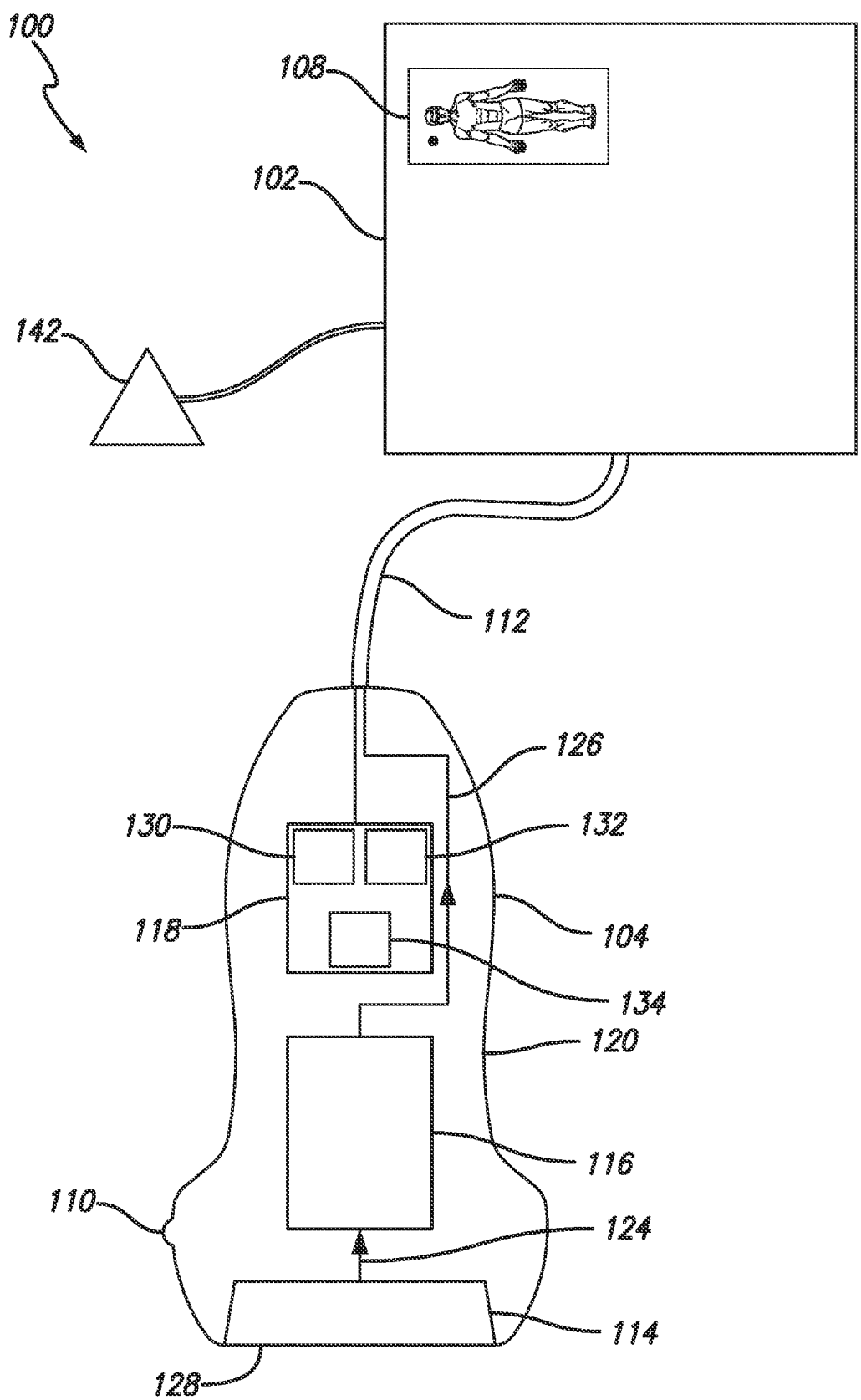
FIG. 1 is a schematic of an embodiment of the disclosed ultrasound system.
Figure 2:
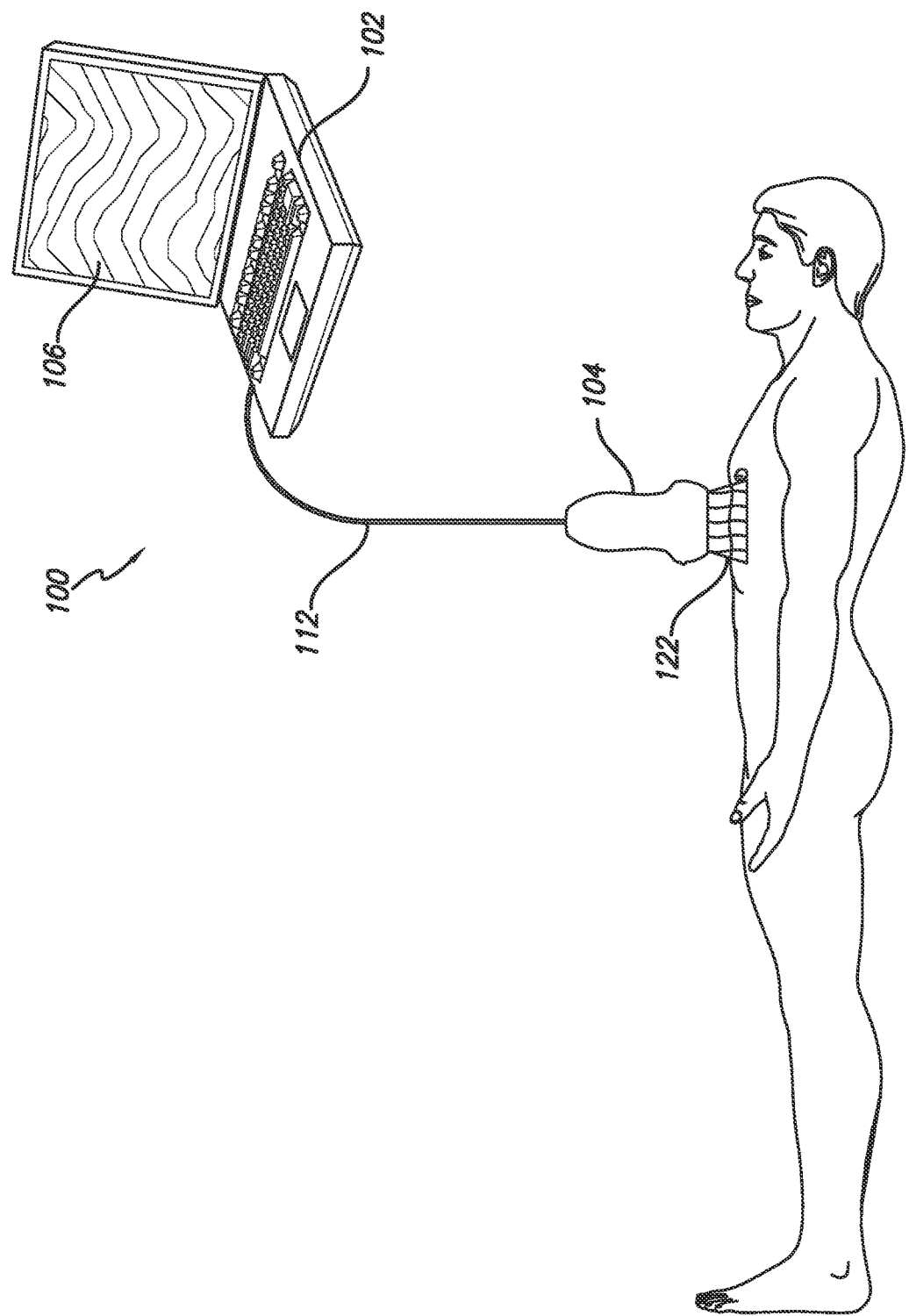
FIG. 2 is a schematic of an embodiment of the disclosed ultrasound system shown in standard mode, where the ultrasound probe is used to scan a real patient.
Figure 3:
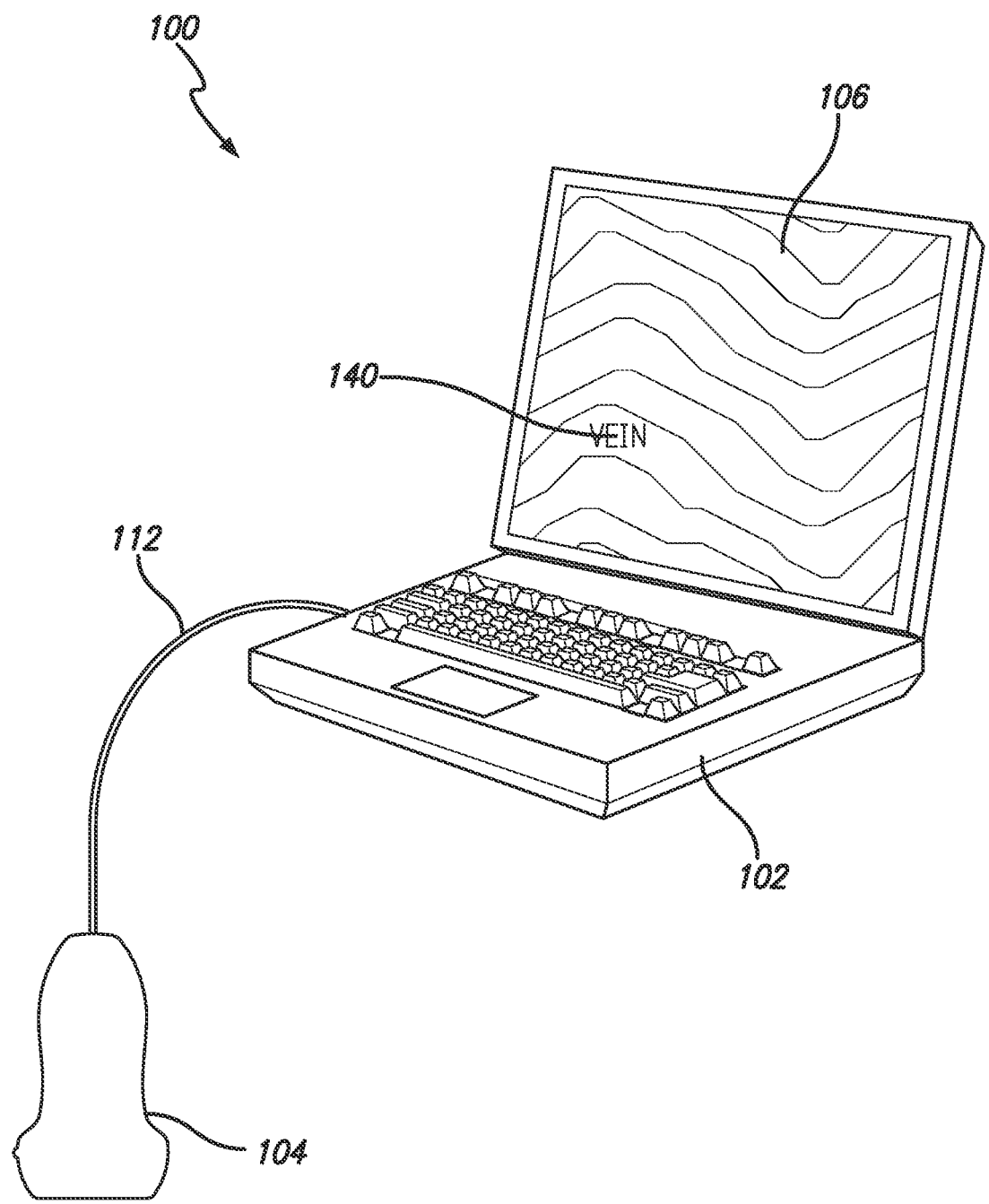
FIG. 3 is a schematic of an embodiment of the disclosed ultrasound system shown in training mode, where the same ultrasound probe as shown in FIG. 2 is now is used as a motion sensing peripheral to navigate existing patient cases.
Figure 4:
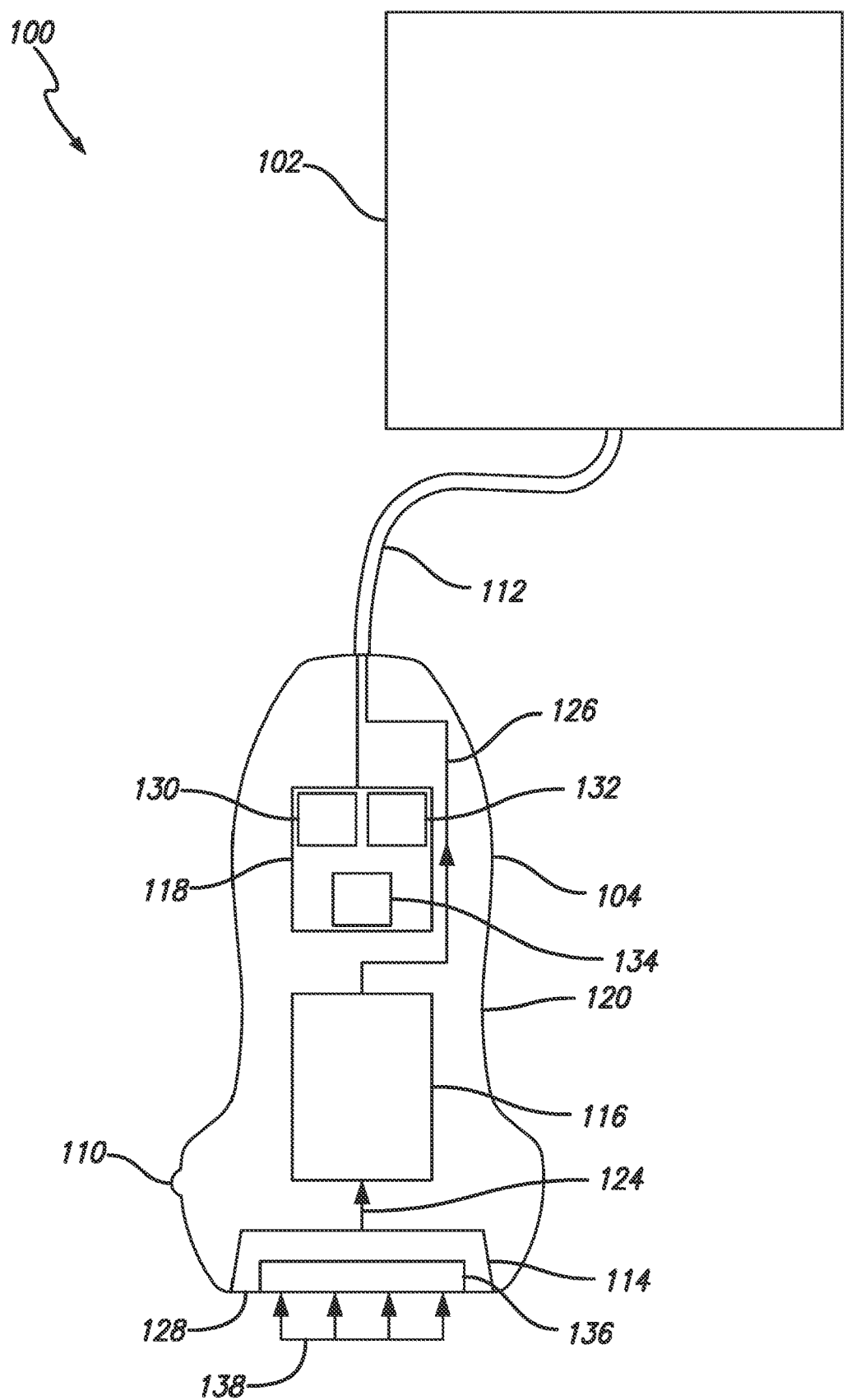
FIG. 4 is a schematic of an embodiment of the disclosed ultrasound system that includes a compression sensor.

The detailed description set forth below in connection with the appended drawings is intended as a description of presently-preferred embodiments of the invention and is not intended to represent the only forms in which the present invention may be constructed or utilized. The description sets forth the functions and the sequence of steps for constructing and operating the invention in connection with the illustrated embodiments. However, it is to be understood that the same or equivalent functions and sequences may be accomplished by different embodiments that are also intended to be encompassed within the spirit and scope of the invention.

The ultrasound system 100 includes an ultrasound machine 102 and an ultrasound probe 104. The ultrasound machine 102 displays an ultrasound image 106. In a version of the invention, the image displayed by the ultrasound machine 102 includes a probe indicator icon 108. In another embodiment, the ultrasound probe 104 also includes a reference indicator 110, which is a direction indicator to orient the ultrasound probe 104.

The ultrasound probe 104 communicates with the ultrasound machine 102. In a version of the invention, the ultrasound probe 104 communicates with the ultrasound machine 102 through a data cable 112. In other versions, the communication is wireless.

The ultrasound probe 104 includes an ultrasound transducer 114, ultrasound circuitry 116, a six degree of freedom (6-DOF) sensor 118, and a probe housing 120. The probe housing 120 encases the ultrasound transducer 114 and the 6-DOF sensor 118.

The ultrasound transducer 114 transmits acoustic waves 122 and measures the reflected acoustic waves 122 to produce a reflected wave signal 124. The ultrasound circuitry 116 receives the reflected wave signal 124 from the ultrasound transducer 114 and transmits an image signal 126 to the ultrasound machine 102. The 6-DOF sensor 118 measures the position and orientation of the ultrasound probe 104.

Preferably, the 6-DOF sensor 118 is an inertial sensor. In an embodiment, the 6-DOF sensor 118 includes an accelerometer 130, a gyroscope 132, and a magnetometer 134. The 6-DOF sensor 118 can be used to detect misalignment and provide a visual alert (for example, in conjunction with the probe indicator icon 108) or an auditory alert to the user about the reference indicator 110 alignment.

In a version of the invention, the ultrasound probe 104 also includes a sensing head 128 at which the ultrasound transducer 114 transmits acoustic waves 122 and measures reflected waves.

In a preferred version, the ultrasound probe 104 also includes a compression sensor 136 that measures the force 138 applied to the sensing head 128. In that version, the probe housing 120 also encases the compression sensor 136. The compression sensor 136 allows the user to investigate the elastic properties of the underlying anatomy in the simulated environment by pressing the tip of the device (for example, the sensing head 128) against a surface with varying amounts of force 138. Preferably, the compression sensor 136 is a resistive strain gauge or other mechanical means that will not interfere with the operation of the ultrasound transducer 114. If the compression sensor 136 interferes with the operation of the ultrasound transducer 114, in some versions the compression sensor 136 may be disabled mechanically when the ultrasound system 100 is operated in the standard mode. In an alternative embodiment, the ultrasound transducer 114 (which is typically built using a highly sensitive piezoelectric element) can itself be used to measure compression directly without a separate compression sensor 136.

With motion-sensing technology embedded directly within the probe housing 120, the ultrasound system 100 can operate in two separate modes: a standard mode that allows the user to use the ultrasound probe 104 to scan real patients using the traditional physics of ultrasound as is done currently, and a training mode that will instead allow the user to employ the same ultrasound probe 104 as a motion sensing peripheral to navigate existing patient cases, perhaps augmented with annotations 140 that help the operator expand and refine his or her knowledge of ultrasound imaging.

More specifically, an ultrasound system 100 equipped with this novel kind of ultrasound probe 104 allows the machine to provide an additional mode of operation for training (training mode). When the training mode is enabled, the user can move the ultrasound probe 104 on the patient's body, a medical mannequin, or other arbitrary surface to navigate a pre-recorded patient case. The software loaded on the ultrasound machine 102 will respond to the motion of the ultrasound transducer 114 in a simulated environment in the same manner as when operating the ultrasound machine 102 in traditional mode (standard mode) with the real physics of ultrasound. The added benefit of the training mode is that the ultrasound operator can correlate what is observed in the real patient with a large library of pre-recorded real and simulated ultrasound cases that may exhibit a wide range of known pathologies. Furthermore, pre-recorded real and simulated ultrasound data may be augmented with additional anatomical annotations 140 that provide further insight on the details of how to use ultrasound imaging in the clinical setting. Those anatomical annotations 140 may include the labeling of pathologies or anatomical structures that are visible in the ultrasound data.

Accordingly, the disclosed solution can mitigate human error that arises from misalignment of the transducer's reference indicator 110 thorough manual and automatic misalignment detection.

Manual misalignment detection—The ultrasound operator can validate the appearance of a desired anatomical region with a pre-recorded case and verify that he or she oriented the ultrasound probe 104 correctly when scanning a patient. This approach does not need any additional equipment or modification beyond the disclosed embedded motion sensor.

More specifically, to calibrate the system, the user places the ultrasound probe 104 at a known position with respect to the ultrasound machine 102. This is necessary to track the position of the ultrasound probe 104 with respect to the ultrasound machine 102 without the aid of any additional sensor or technology. The ultrasound machine 102 provides the user with an on-screen visual reference to establish how the sensor should be aligned (for example, with the probe indicator icon 108). AU existing ultrasound machines provide such reference in the form of a small colored circle on the side of the screen. For the disclosed application it may be also useful, but not necessary, to show a visual representation of the patient's body on-screen to provide additional guidance.

The ultrasound operator may then scan the patient's body, a medical mannequin, or other arbitrary surface. The embedded 6-DOF sensor 118 informs the ultrasound machine 102 about the position of the 6-DOF sensor 118 throughout the scanning session.

Software in the ultrasound machine 102 continuously monitors the position and orientation of the ultrasound probe 104 during the scanning session using the readings from the 6-DOF sensor 118. The calibration procedure noted above allows the software to compute the relative position of the 6-DOF sensor 118 with respect to the ultrasound machine 102. If the software detects that the ultrasound probe 104 is not aligned correctly according to established medical conventions, then a visual or audio alert is generated to inform the operator about the hazard.

Automatic misalignment detection—If additional means (as explained below) are available for determining the position of the ultrasound unit with respect to the ultrasound transducer 114, software on the device can determine automatically whether or not the current orientation of the ultrasound transducer 114 is correct by checking if the expected medical conventions are being honored. This solution does not require a separate calibration step, and it may be more accurate over the extent of the scanning session.

More specifically, this approach requires two-point motion sensing solution where a reference beacon 142 is placed at fixed position on the ultrasound machine 102 and the receiver is placed inside the ultrasound probe, preferably as part of the 6-DOF sensor 118. During the ultrasound scanning process, the two-point sensor solution informs the ultrasound machine 102 about the position of the 6-DOF sensor 118 relative to the ultrasound machine 102 throughout the scanning session. Software on the ultrasound machine 102 continuously monitors the position and orientation of the ultrasound probe 104 with respect to the ultrasound machine 102 during the scanning session using the readings from the two-point sensor solution (that is, the reference beacon 142 in conjunction with the 6-DOF sensor 118). If the software detects that the ultrasound probe 104 is not aligned correctly according to established medical conventions, then a visual or audio alert is generated to inform the operator about the hazard.

While the present invention has been described with regards to particular embodiments, it is recognized that additional variations of the present invention may be devised without departing from the inventive concept.

INDUSTRIAL APPLICABILITY

This invention may be industrially applied to the development, manufacture, and use of ultrasound probes, ultrasound probe systems, and ultrasound probe training systems.

What is claimed is:

1. An embedded ultrasound training system, the ultrasound training system having a standard mode and a training mode, the ultrasound training system comprising:
   (a) an ultrasound machine configured to operate in the standard mode and the training mode;
   (b) an ultrasound probe operatively connected to the ultrasound machine, the ultrasound probe comprising:
      (i) a sensing head;
      (ii) an ultrasound transducer that, when operated, transmits acoustic waves from and measures reflected waves received at the sensing head to produce a reflected wave signal,
      (iii) ultrasound circuitry, the ultrasound circuitry configured to receive the reflected wave signal from the ultrasound transducer and transmitting an image signal to the ultrasound machine,
      (iv) an inertial sensor, the inertial sensor configured for measuring a position and an orientation of the ultrasound probe; and
      (v) a probe housing encasing the ultrasound transducer, the inertial sensor, and a compression sensor; and
   (c) a library of pre-recorded ultrasound cases connected to the training mode to simulate the functioning of the ultrasound probe as if in the standard mode, wherein when the ultrasound transducer is active in the standard mode, a user can scan a patient through transmitted acoustic waves and reflected waves, and wherein when the ultrasound transducer is inactive in the training mode, the ultrasound probe functions as a motion sensing peripheral in a simulated environment to navigate the library of pre-recorded ultrasound cases, whereby, the position and the orientation of the ultrasound probe are displayed on the ultrasound machine.

2. The ultrasound system of claim 1, where the ultrasound transducer is a piezoelectric element.

3. An ultrasound system, comprising:
   (a) an ultrasound machine configured for operating in a standard mode and a training mode; and
   (b) an ultrasound probe operatively connected to the ultrasound machine, the ultrasound probe comprising:
      (i) an ultrasound transducer configured for transmitting acoustic waves and measuring reflected waves to produce a reflected wave signal,
      (ii) ultrasound circuitry configured for receiving the reflected wave signal from the ultrasound transducer and configured for transmitting an image signal to the ultrasound machine,
      (iii) a motion sensor configured for measuring a position and an orientation of the ultrasound probe, and
      (iv) a probe housing encasing the ultrasound transducer, wherein the ultrasound transducer is configured for scanning a patient in the standard mode, and wherein the ultrasound probe is configured for use as a motion sensing peripheral in the training mode.

4. The ultrasound system of claim 3, further comprising a library of pre-recorded ultrasound cases connected to the training mode to simulate the functioning of the ultrasound probe as if in the standard mode.

5. The ultrasound system of claim 3, wherein the ultrasound probe further includes a reference indicator, the reference indicator comprising a direction indicator to orient the ultrasound probe.

6. The ultrasound system of claim 3, wherein the ultrasound probe further includes a sensing head at which the ultrasound transducer transmits the acoustic waves and measures the reflected waves.

7. The ultrasound system of claim 6, wherein the ultrasound transducer is configured to measure a force on the sensor head.

8. The ultrasound system of claim 7, wherein the ultrasound transducer comprises a piezoelectric element.

9. The ultrasound system of claim 3, wherein the motion sensor is an inertial sensor.

10. The ultrasound system of claim 3, wherein the motion sensor comprises an accelerometer.

11. The ultrasound system of claim 3, wherein the ultrasound probe further comprises a compression sensor that measures a force on the ultrasound probe, and the probe housing encases the compression sensor.

12. The ultrasound system of claim 11, where the compression sensor comprises a resistive strain gauge.

13. A method, comprising the steps of:
  (a) providing an ultrasound machine configured for operating in a standard mode and providing a training mode; and providing an ultrasound probe operatively connected to the ultrasound machine, the ultrasound probe comprising:
    (i) an ultrasound transducer configured for transmitting acoustic waves and measuring reflected waves to produce a reflected wave signal,
    (ii) ultrasound circuitry configured for receiving the reflected wave signal from the ultrasound transducer and configured for transmitting an image signal to the ultrasound machine,
    (iii) a motion sensor configured for measuring a position and an orientation of the ultrasound probe, and
    (iv) a probe housing encasing the ultrasound transducer, wherein the ultrasound transducer is configured for scanning a patient in the standard mode, and wherein the ultrasound probe is configured for use as a motion sensing peripheral in the training mode; and
  (b) using the ultrasound system in the standard mode by:
    (i) activating the ultrasound transducer,
    (ii) operating the ultrasound probe to scan the patient, the ultrasound transducer transmitting the acoustic waves and measuring the reflected waves to produce the reflected wave signal,
    (iii) the ultrasound circuitry receiving the reflected wave signal from the ultrasound transducer and transmitting the image signal to the ultrasound machine, and
    (iv) the ultrasound machine displaying an ultrasound image.

14. The method of claim 13, further comprising using the ultrasound system in the training mode by switching to the training mode from the standard mode, measuring a position and orientation of the ultrasound probe, and employing the ultrasound probe as the motion sensing peripheral to navigate a library of pre-recorded ultrasound cases based on the measured position and orientation of the ultrasound probe.

15. The method of claim 14, wherein the step of using the ultrasound system in the training mode further comprises coordinating a probe indicator icon to the motion sensor such that the probe indicator icon moves in a coordinated fashion to a reference indicator of the ultrasound probe, and the library of pre-recorded ultrasound cases responds to the measured position and orientation of the ultrasound probe.

16. The method of claim 15, wherein the step of coordinating the probe indicator icon in relation to the inertial sensor comprises wirelessly coupling the motion sensor to a reference beacon connected to the ultrasound training system.

17. The method of claim 15, further comprising the steps of:
  (a) detecting a misalignment between the probe indicator icon and the reference indicator; and
  (b) providing an alert to a user about the detected misalignment.

18. The method of claim 17, wherein the alert is visual.

19. The method of claim 17, wherein the alert is auditory.

20. The method of claim 14, wherein the step of using the ultrasound system in the training mode further comprises the step of augmenting the library of pre-recorded ultrasound cases with one or more anatomical annotations before navigating the library of pre-recorded ultrasound cases.

* * * * *